United States Patent
Huh et al.

(10) Patent No.: US 8,018,595 B2
(45) Date of Patent: Sep. 13, 2011

(54) APPARATUS FOR DETECTING BIO MATERIALS AND METHOD FOR DETECTING BIO MATERIALS BY USING THE APPARATUS

(75) Inventors: Chul Huh, Daejeon (KR); Kyung Hyun Kim, Daejeon (KR); Hyunsung Ko, Seoul (KR); Wanjoong Kim, Goyang (KR); Gun Yong Sung, Daejeon (KR); Seon-Hee Park, Daejeon (KR); Bong-Kyu Kim, Daejeon (KR)

(73) Assignee: Electronics and Telecommunications Research Institute, Daejeon (KR)

(*) Notice: Subject to any disclaimer, the term of this patent is extended or adjusted under 35 U.S.C. 154(b) by 353 days.

(21) Appl. No.: 12/406,851

(22) Filed: Mar. 18, 2009

(65) Prior Publication Data

US 2010/0134799 A1 Jun. 3, 2010

(30) Foreign Application Priority Data

Dec. 3, 2008 (KR) .................. 10-2008-0121780

(51) Int. Cl.
*G01N 21/00* (2006.01)
(52) U.S. Cl. .................. 356/432; 356/436; 436/528
(58) Field of Classification Search .......... 356/432–440, 356/326; 435/5, 6, 7.1, 7.9, 91.2; 436/72, 436/81, 83, 528
See application file for complete search history.

(56) References Cited

U.S. PATENT DOCUMENTS

| 7,129,096 B2 | 10/2006 | Chilkoti et al. |
| 7,830,507 B2 * | 11/2010 | Brady et al. ............... 356/328 |
| 2005/0019842 A1 | 1/2005 | Prober et al. |
| 2010/0141942 A1 * | 6/2010 | Kim et al. ............... 356/326 |

FOREIGN PATENT DOCUMENTS

| KR | 1020050073609 A | 7/2005 |
| KR | 1020070105568 A | 10/2007 |
| WO | WO 2004/044232 A1 | 5/2004 |

OTHER PUBLICATIONS

Nidhi Nath et al., "A Colorimetric Gold Nanoparticle Sensor to Interrogate Biomolecular Interactions in Real Time on a Surface," Analytical Chemistry, Feb. 1, 2002, pp. 504-509, vol. 74, No. 3.

* cited by examiner

*Primary Examiner* — Hoa Q Pham

(57) ABSTRACT

Provided is an apparatus for detecting bio materials and a method for detecting bio materials by using the apparatus. The apparatus includes a bio material reacting unit, an optical source unit, and a detecting unit. The bio material reacting unit includes bio sensing materials immobilized on gold nanoparticles. The optical source unit emits light toward the bio material reacting unit. The detecting unit measures variations of surface absorbance of the gold nanoparticles by detecting light transmitted through the bio material reacting unit before and after a bio material is bound to the bio sensing materials.

19 Claims, 6 Drawing Sheets

APPARATUS FOR DETECTING BIO MATERIALS AND METHOD FOR DETECTING BIO MATERIALS BY USING THE APPARATUS

CROSS-REFERENCE TO RELATED APPLICATIONS

This U.S. non-provisional patent application claims priority under 35 U.S.C. §119 of Korean Patent Application No. 10-2008-0121780, filed on Dec. 3, 2008, the entire contents of which are hereby incorporated by reference.

BACKGROUND OF THE INVENTION

The present invention disclosed herein relates to an apparatus for detecting bio materials and a method for detecting bio materials by using the apparatus, and more particularly, to an apparatus and method for detecting bio materials by measuring surface absorbance variations of gold nanoparticles.

Biosensors are used to detect an optical or electric signal varying according to selective reaction and binding between an analysis-target assay and a biological receptor capable of recognizing a specific bio material. That is, biosensors are used to determine the existence of a bio material or analyze a bio material qualitatively or quantitatively. Materials such as enzymes, antibodies, and DNAs that can selectively react or couple with specific materials are used as biological receptors (i.e., sensing materials). Various physicochemical methods, such as a method of detecting an electric signal varying according to the existence of an assay and a method of detecting an optical signal varying according to a chemical reaction between a receptor and an assay, are used as signal detection methods for detecting and analyzing bio materials.

In a typical bio material detection method (label detection method), a specific antibody is labeled with a material such as a radioisotope or a fluorescent material, and then a corresponding antigen is quantitatively detected by measuring variations of radiation or fluorescence caused by a reaction between the specific antibody and the corresponding antigen. However, such a bio material detection method requires complicated processes and high process costs due to, for example, an additional process necessary for labeling a specific antibody with a fluorescent material emitting a specific color.

Therefore, recent research has been conducted on a label-free detection method that does not use a label material such as a fluorescent material emitting a specific color. That is, much research has been conducted on optical biosensors such as a surface plasmon biosensor, a total internal reflection ellipsometry biosensor, and an optical waveguide biosensor.

Generally, such label-free optical biosensors using surface plasmon, total internal reflection, or an optical waveguide are configured by an optical source unit capable of emitting light, a reacting unit adapted for reacting antibodies and antigens, and an optical detecting unit adapted for detecting an optical signal. Generally, a device such as a light-emitting diode and a laser is used as the optical source unit, and a spectrometer is used as the optical detecting unit.

However, in the case of using a spectrometer as the optical detecting unit, the sensitivity of the optical detecting unit may vary largely according to the direction of light incident on the reacting unit. Furthermore, to measure an optical spectrum, the optical source unit should be a frequency variable optical source unit, or the optical detecting unit used to detect variations of an optical signal should be a spectrometer. Therefore, very complicated optical systems are required for configuring the optical source unit and the optical detecting unit, and thus the manufacturing costs of a biosensor increase.

SUMMARY OF THE INVENTION

The present invention provides an apparatus for detecting bio materials more easily.

The present invention also provides a method for detecting bio materials more easily.

The object of the present invention is not limited to the aforesaid, but other objects not described herein will be clearly understood by those skilled in the art from descriptions below.

Embodiments of the present invention provide apparatuses for detecting bio materials, the apparatus including: a bio material reacting unit including bio sensing materials immobilized on gold nanoparticles; an optical source unit configured to emit light toward the bio material reacting unit; and a detecting unit configured to measure variations of surface absorbance of the gold nanoparticles by detecting light transmitted through the bio material reacting unit before and after a bio material is bound to the bio sensing materials.

In other embodiments of the present invention, there is provided methods for detecting bio materials, the method including: immobilizing bio sensing materials capable of binding to a bio material on gold nanoparticles; binding bio materials to the bio sensing materials immobilized on the gold nanoparticles; illuminating light onto the gold nanoparticles before the binding of the bio materials to the bio sensing materials; illuminating light onto the gold nanoparticles after the binding of the bio materials to the bio sensing materials; and measuring variations of surface absorbance of the gold nanoparticles by detecting light transmitted through the gold nanoparticles before and after the binding of the bio materials to the bio sensing materials.

The details of other embodiments are included in the detailed description and the drawings.

BRIEF DESCRIPTION OF THE FIGURES

The accompanying figures are included to provide a further understanding of the present invention, and are incorporated in and constitute a part of this specification. The drawings illustrate exemplary embodiments of the present invention and, together with the description, serve to explain principles of the present invention. In the figures.

DETAILED DESCRIPTION OF PREFERRED EMBODIMENTS

Figure 1:
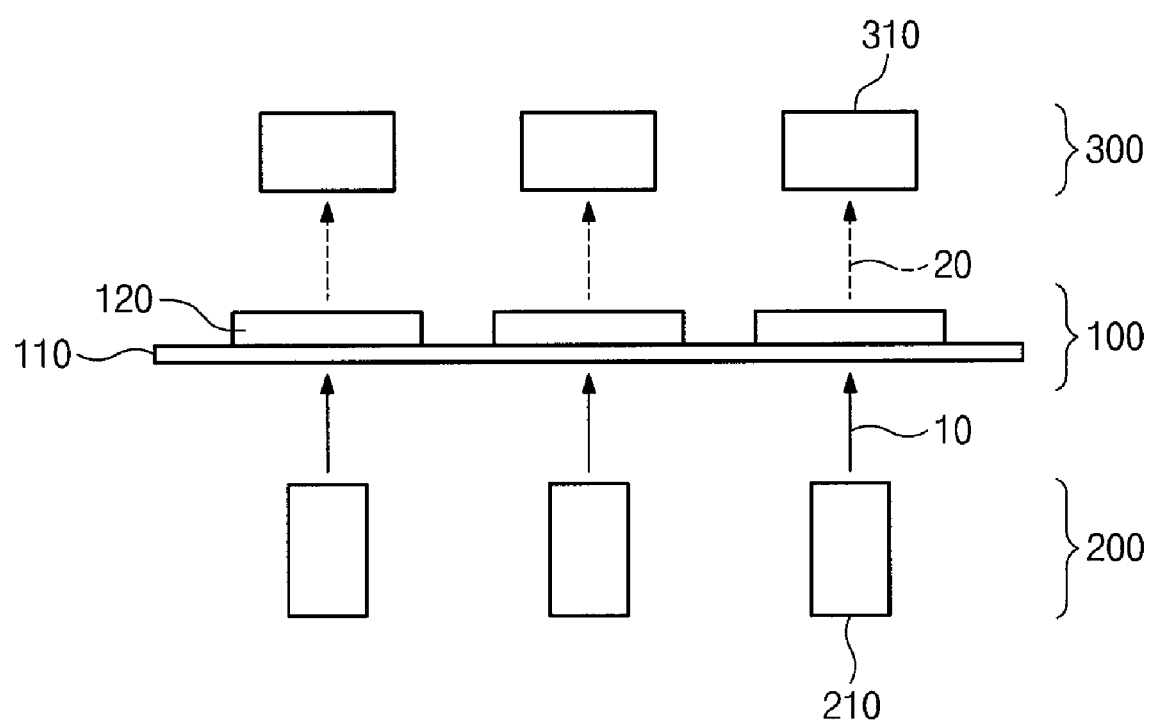
FIG. 1 is a schematic view illustrating an apparatus for detecting bio materials according to an embodiment of the present invention.

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. Like reference numerals refer to like elements throughout.

In the following description, the technical terms are used only for explaining specific exemplary embodiments while not limiting the present invention. The terms of a singular form may include plural forms unless otherwise specified. The meaning of "include," "comprise," "including," or "comprising," specifies a property, a region, a fixed number, a step, a process, an element and/or a component but does not exclude other properties, regions, fixed numbers, steps, processes, elements and/or components.

Additionally, the embodiments in the detailed description will be described with sectional views or plan views as ideal exemplary views of the present invention. In the drawings, the dimensions of layers and regions are exaggerated for clarity of illustration. Areas exemplified in the drawings have general properties, and are used to illustrate specific shapes of device regions. Thus, these should not be construed as limiting to the scope of the present invention.

In the specification, the term "gold nanoparticles(s)" is used to denote gold nanoparticles having a size in the range from about 1 nm to about 1000 nm. That is, in the embodiments of the present invention, gold nanoparticles have a diameter in the range from about 1 nm to about 1000 nm.

In the specification, the term "bio material(s)" is used to denote biological molecules exhibiting a specific nature and may be interpreted as having the same meaning as target molecules, assays, or analytes.

In the specification, the term "bio sensing material(s)" is used to denote bio molecules specifically binding to a bio material and may be interpreted as having the same meaning as probe molecules, receptors, or acceptors.

Hereinafter, a detailed description will be given on an apparatus for detecting bio materials with reference to the accompanying drawings according to exemplary embodiments of the present invention.

Figure 2:
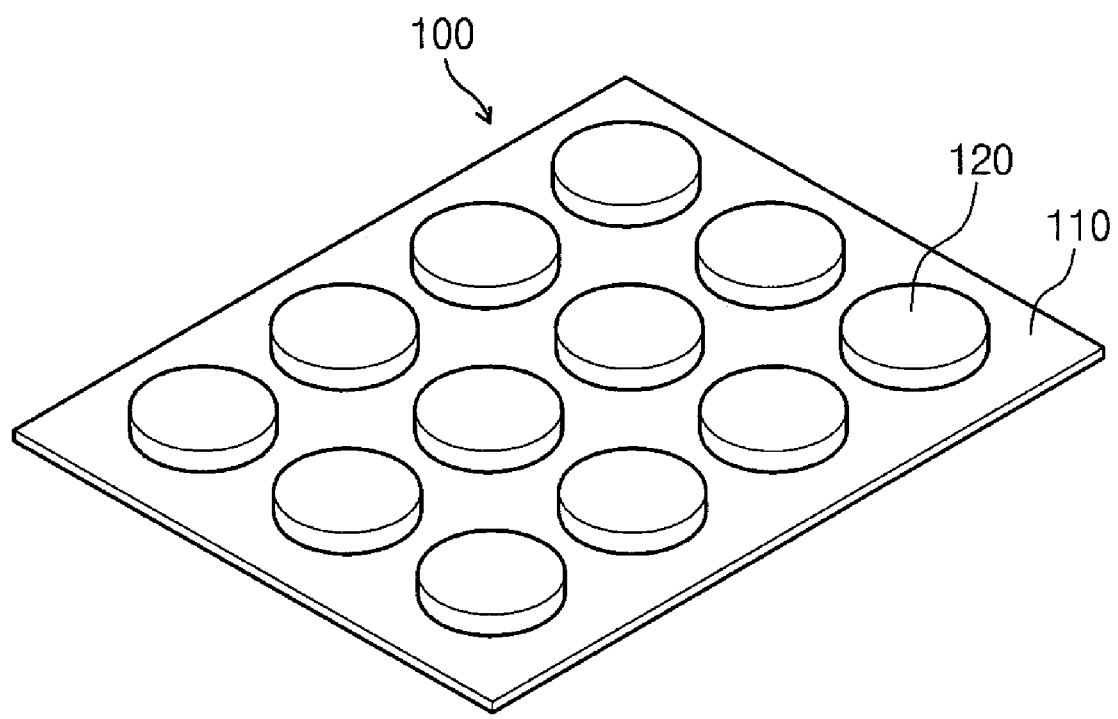
FIG. 2 is a schematic perspective view illustrating a bio material reacting unit of the bio material detecting apparatus according to an embodiment of the present invention.

FIG. 1 is a schematic view illustrating an apparatus for detecting bio materials according to an embodiment of the present invention, and FIG. 2 is a schematic perspective view illustrating a bio material reacting unit 100 of the bio material detecting apparatus according to an embodiment of the present invention.

Referring to FIG. 1, the bio material detecting apparatus of the current embodiment includes the bio material reacting unit 100, an optical source unit 200, and a detecting unit 300.

As shown in FIG. 2, the bio material reacting unit 100 includes a substrate 110 and reaction vessels 120 disposed at the substrate 110.

The substrate 110 may be formed of a transparent material to transmit light. For example, the substrate 110 may be a plastic, glass, or silicon substrate. Alternatively, the substrate 110 may be a transparent oxide substrate formed of a material such as a titanium oxide ($TiO_2$), a tantalum oxide ($Ta_2O_5$), or an aluminum oxide ($Al_2O_3$). Alternatively, the substrate 110 may be formed of a transparent polymer such as polydimethylsiloxane (PDMS), polymethylmethacrylate (PMMA), polycarbonate (PC), cyclic olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), or perfluoralkoxyalkane (PFA).

The reaction vessels 120 may be disposed at a plurality of positions of the substrate 110, and bio sensing structures are accommodated in the reaction vessels 120. In an embodiment of the present invention, the term "bio sensing structure(s)" is used to denote bio sensing materials immobilized on the surfaces of gold nanoparticles, and analysis-target bio materials may specifically bind to the bio sensing structures. According to the size of the gold nanoparticles of the bio sensing structures and the kind of materials immobilized on the gold nanoparticles, the wavelength of light incident on the gold nanoparticles may be varied, and the amount of light absorbed on the surfaces of the gold nanoparticles may be varied. In detail, the surface absorbance of the gold nanoparticles is varied according to the size of the gold nanoparticles by the surface plasmon effect. The bio sensing materials are materials to which detection and analysis target bio materials can bind specifically (selectively). For example, the bio sensing materials may be proteins, cells, viruses, nucleic acids, organic molecules, or non-organic molecules. Examples of proteins that can be the bio sensing materials include any proteins such as antigens, antibodies, matrix proteins, enzymes, and coenzymes. Examples of nucleic acids that can be the bio sensing materials include DNAs, RNAs, PNAs, LNAs, or hybrids thereof.

Bio materials may be put into the reaction vessels 120 from the outside to react the bio materials with the bio sensing structures provided in the reaction vessels 120. That is, in the reaction vessels 120, bio materials may bind to or react with the bio sensing structures. Alternatively, a buffer solution may be filled in the reaction vessels 120, and in this case, the bio sensing structures may be dispersed throughout the buffer solution in the reaction vessels 120. For example, the buffer solution may be water or a phosphate buffered saline (PBS) solution.

Bio sensing structures having different characteristics may be accommodated in the reaction vessels 120. In this case, bio materials having the same or different characteristics may be disposed into the respective reaction vessels 120. Therefore, by putting a solution containing various bio materials into the respective reaction vessels 120, the various bio materials can be detected at a time.

The optical source unit 200 emits light 10 toward the bio material reacting unit 100, that is, toward the gold nanoparticles of the bio material reacting unit 100. The optical source unit 200 may include a plurality of optical sources 210 according to the number of the reaction vessels 120 of the bio material reacting unit 100.

In an embodiment of the present invention, the number of the optical sources 210 may be equal to the number of the reaction vessels 120. In another embodiment of the present invention, it may be configured in a manner such that light 10 is emitted from one optical source 210 toward a plurality of reaction vessels 120.

Light 10 emitted from the optical source unit 200 may be absorbed on the surfaces of the gold nanoparticles, and the amount of the light 10 absorbed on the surfaces of the gold nanoparticles may be varied according to materials located around or on the surfaces of the gold nanoparticles. As the light 10 emitted from the optical source unit 200 is absorbed by the gold nanoparticles, the intensity of the light 10 may be accordingly varied. The surface absorbance of the gold nanoparticles may be varied according to bio sensing materials and bio materials that are disposed on the surfaces of the gold nanoparticles.

Light emitting diodes may be used as the optical sources 210 of the optical source unit 200, and the wavelength of the optical sources 210 may vary according to the size of the gold nanoparticles.

The detecting unit 300 detects light 20 transmitted through the bio material reacting unit 100 to measure variations of the surface absorbance of the gold nanoparticles before and after bio materials are bound to bio sensing materials. The detecting unit 300 may include optical sensing devices 310 (i.e., optical sensors) for measuring the surface absorbance of the gold nanoparticles by sensing the amount or intensity of light 20 transmitted through the bio material reacting unit 100. The surface absorbance of the gold nanoparticles may be varied according to the surrounding environment or materials of the gold nanoparticles by the surface plasmon resonance effect. That is, bio materials can be detected and analyzed by detecting variations of the surface absorbance of the gold nanoparticles.

The detecting unit 300 is configured by an optical detector most sensitive to the wavelength of light, which is emitted from the optical source unit 200 and transmitted through the bio material reacting unit 100. For example, the detecting unit 300 may be configured by an imaging device such as a photodiode, a phototransistor, a photomultiplier, a charge coupled device (CCD), or a complementary metal oxide semiconductor (CMOS) image sensor.

Hereinafter, a method for detecting bio materials and a method for detecting concentrations of bio materials will be described in detail with reference to FIGS. 3, 4, 5A, 5B, and 5c according to embodiments of the present invention.

Figure 3:
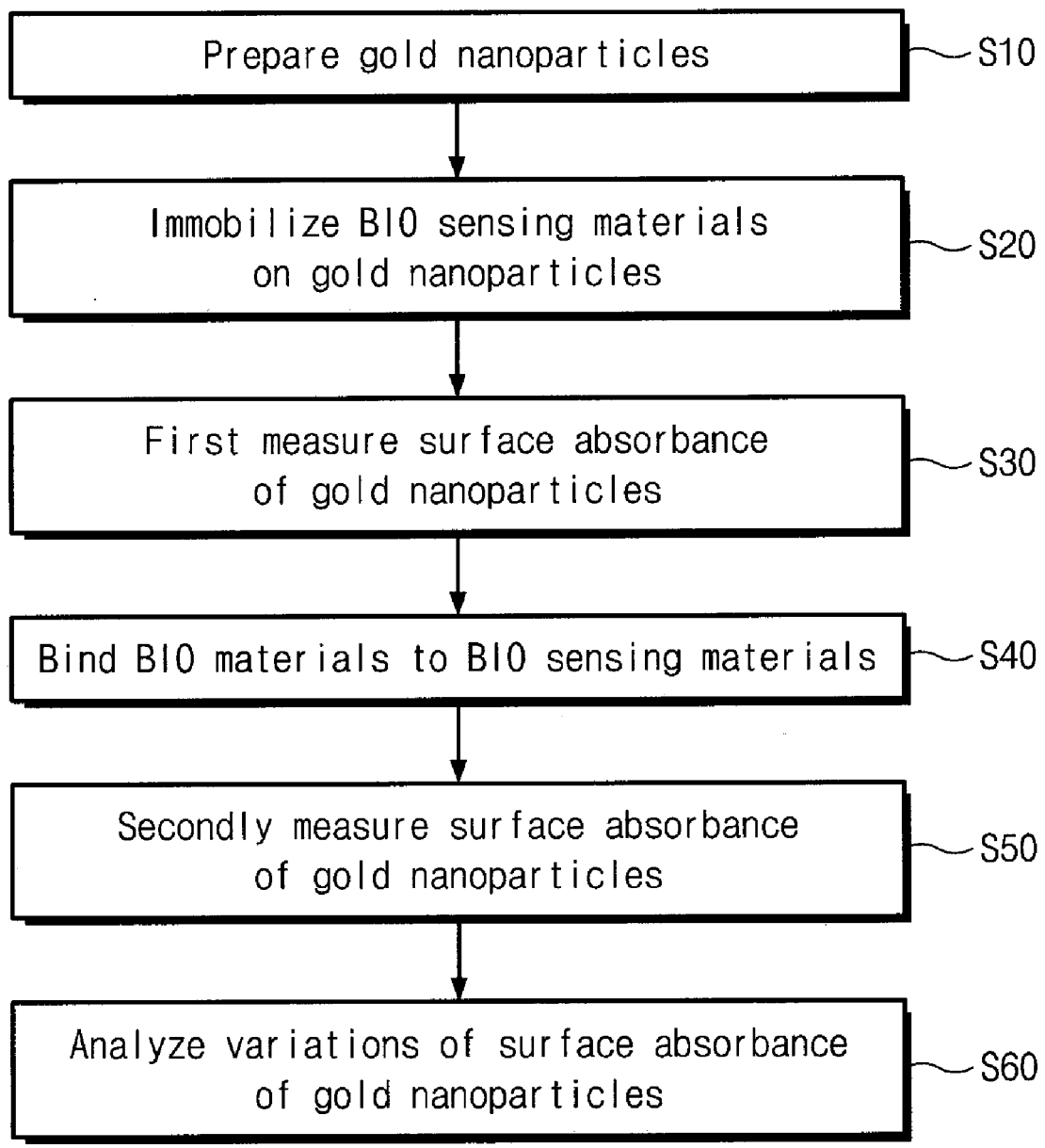
FIG. 3 is a flowchart for explaining a method for detecting bio materials according to an embodiment of the present invention.
Figure 4:
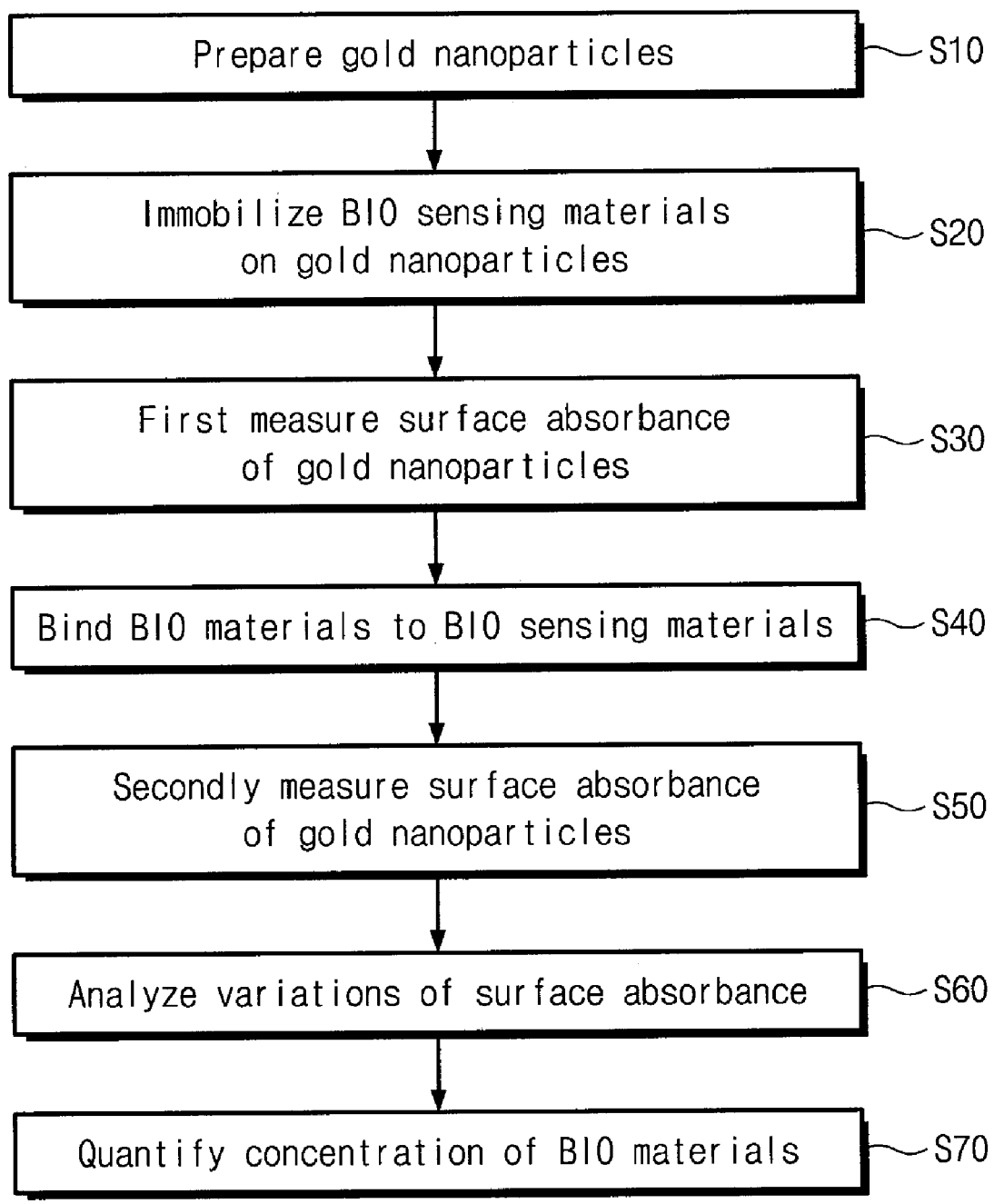
FIG. 4 is a flowchart for explaining a method for measuring concentrations of bio materials according to an embodiment of the present invention.
Figure 5A:
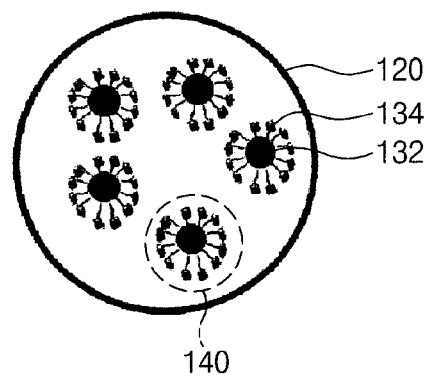
FIGS. 5A through 5C are schematic views illustrating variations of gold nanoparticles caused by binding between bio sensing materials and bio materials in a method for detecting bio materials according to an embodiment of the present invention.
Figure 5B:
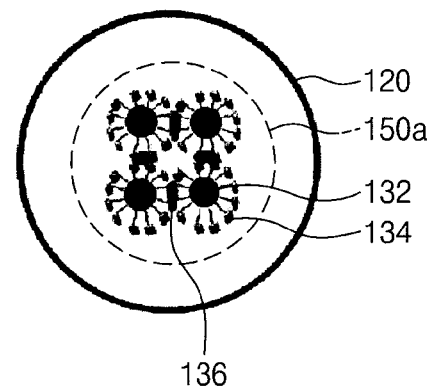
Figure 5C:
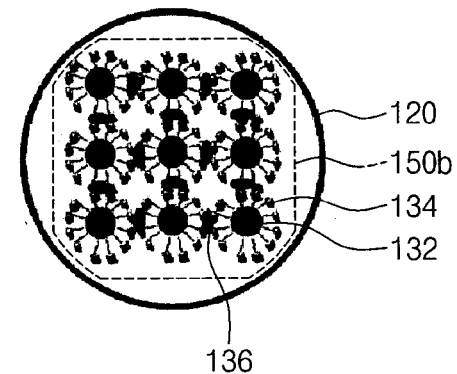

FIG. 3 is a flowchart for explaining a method for detecting bio materials according to an embodiment of the present invention, and FIG. 4 is a flowchart for explaining a method for measuring concentrations of bio materials according to an embodiment of the present invention. FIGS. 5A through 5C are schematic views illustrating variations of gold nanoparticles caused by binding between bio sensing materials and bio materials in a method for detecting bio materials according to an embodiment of the present invention.

Referring to FIGS. 3 and 5A, gold nanoparticles 132 are prepared by a typical method in operation S10. For example, gold nanoparticles 132 having a nano scale size may be prepared by a physical, chemical, or electrolysis method.

The surface absorbance of the gold nanoparticles 132 is varied according to the size of the gold nanoparticles by the surface plasmon effect. The surface plasmon effect means that when light having a particular wavelength is irradiated to the surface of gold, electrons existing at the surface of the gold are oscillated to generate waves (surface plasmon waves). Oscillation of quantized electrons is called "surface plasmon." The wavelength of surface plasmon waves is varied according to materials disposed on the surface of gold. For the same reason, the surface absorbance of the gold nanoparticles varies.

After the gold nanoparticles 132 are prepared, bio sensing materials 134 are immobilized on the surfaces of the gold nanoparticles 132 to form bio sensing structures 140 (operation S20).

The bio sensing materials 134 immobilized on the surfaces of the gold nanoparticles 132 may be proteins, cells, viruses, nucleic acids, organic molecules, or non-organic molecules according to the kind of bio materials to be detected. Examples of proteins that can be the bio sensing materials 134 include any proteins such as antigens, antibodies, matrix proteins, enzymes, and coenzymes. Examples of nucleic acids that can be the bio sensing materials 134 include DNAs, RNAs, PNAs, LNAs, or hybrids thereof.

The bio sensing materials 134 may be immobilized on the surfaces of the gold nanoparticles 132 by a method such as chemical adsorption, covalent-binding, electrostatic attraction, co-polymerization, or avidin-biotin affinity binding.

The bio sensing materials 134 may be immobilized on the surfaces of the gold nanoparticles 132 directly or through intermediate molecules such as organic molecules. Functional groups can be formed on the surfaces of the gold nanoparticles 132 to immobilize the bio sensing materials 134 on the surfaces of the gold nanoparticles 132. For example, functional groups such as carboxyl groups (—COOH), thiol groups (—SH), hydroxyl groups (—OH), silane groups, amine groups, or epoxy groups may be formed on the surfaces of the gold nanoparticles 132.

After the bio sensing materials 134 are immobilized on the surfaces of the gold nanoparticles 132, the bio sensing structures 140 are dispersed in the reaction vessels 120 (referring to FIG. 1) of the bio material reacting unit 100 (refer to FIG. 1). In the reaction vessels 120, a buffer solution may be filled, and in this case, the bio sensing structures 140 may be uniformly dispersed throughout the buffer solution. The buffer solution may be water or a PBS solution.

After dispersing the bio sensing structures 140 in the reaction vessels 120, in operation S30, the surface absorbance of the gold nanoparticles 132 is measured using the detecting unit 300 (refer to FIG. 1) (first measurement).

In detail, light is emitted from the optical source unit 200 (refer to FIG. 1) to the reaction vessels 120 of the bio material reacting unit 100, and then, a portion of the light may be absorbed by the gold nanoparticles 132. Thereafter, light transmitted through the gold nanoparticles 132 is detected to measure the surface absorbance of the gold nanoparticles 132. That is, in operation S30, the surface absorbance of the gold nanoparticles 132 is measured when only the bio sensing materials 134 are immobilized on the surfaces of the gold nanoparticles 132. The surface absorbance measured in operation S30 will be referred to as a first surface absorbance.

Next, referring to FIGS. 3, 5B, and 5C, detection-target bio materials 136 are put into the reaction vessels 120 accommodating the bio sensing structures 140 to allow binding of the bio materials 136 to the bio sensing materials 134 (operation S40).

In an embodiment of the present invention, the bio materials 136 are bio molecules obtained from a living body that specifically bind to the bio sensing materials 134. In detail, a solution containing the bio materials 136 is put into the reaction vessels 120 in which the bio sensing materials 134 are immobilized on the gold nanoparticles 132. For example, the solution containing the bio materials 136 may be a body fluid obtained from a living body, such as blood, blood serum, blood plasma, urine, or saliva. Therefore, as well as the detection-target bio materials 136, nonspecific molecules that does not bind to the bio sensing materials 134 may be contained in the solution containing the bio materials 136.

For example, the bio materials 136 may be nucleic acids, cells, viruses, proteins, organic molecules, or non-organic molecules. Examples of proteins that can be the bio materials 136 include any proteins such as antigens, antibodies, matrix proteins, enzymes, and coenzymes. Examples of nucleic acids that can be the bio materials 136 include DNAs, RNAs, PNAs, LNAs, or hybrids thereof.

The bio materials 136 put into the reaction vessels 120 may bind to the bio sensing materials 134 by chemical and biochemical reaction such as nucleic acid hybridization, antigen-antibody reaction, and enzyme binding reaction.

After the bio materials 136 are bound to the bio sensing materials 134 in this way, light is emitted from the optical source unit 200 to the bio material reacting unit 100, and the surface absorbance of the gold nanoparticles 132 is measured using the detecting unit 300 (second measurement) (operation S50)

In detail, light is irradiated to the surfaces of the gold nanoparticles 132 on which the bio sensing materials 134 and the bio materials 136 are bound to each other, so as to measure the surface absorbance of the gold nanoparticles 132. Since the bio materials 136 are bound to the bio sensing structures 140, the surface absorbance of the gold nanoparticles 132 is varied by the surface plasmon effect. The surface absorbance measured in operation S50 will be referred to as a second surface absorbance.

Thereafter, variations of the surface absorbance of the gold nanoparticles 132 are analyzed in operation S60. That is, the existence of the bio materials 136 can be determined according to the variations of the surface absorbance of the gold nanoparticles 132. In detail, the difference between the first and second surface absorbances is calculated. Since materials immobilized on the gold nanoparticles 132 are different between the measurements of the first and second surface absorbances, the first and second surface absorbances are different. Therefore, the bio materials 136 can be detected by measuring the surface absorbance of the gold nanoparticles 132 before and after binding the bio materials 136 to the bio sensing materials 134. In the case where the bio materials 136 do not specifically bind to the bio sensing structures 140, the first and second surface absorbances are not largely different.

Referring to FIG. 4, as well as the existence of bio materials, the concentrations of the bio materials can be measured (operation S70) by detecting variations of the surface absorbance of gold nanoparticles.

This will now be described in more detail with reference to FIGS. 5B and 5C. As time passes after bio materials 136 are put into the reaction vessels 120 accommodating bio sensing structures 140, the bio materials 136 may bind to at least one of bio sensing materials 134. As a result, gold nanoparticles 132 of the reaction vessels 120 may gather to form aggregations 150a and 150b.

The size of the aggregations 150a and 150b formed as a result of binding between the bio sensing materials 134 and the bio materials 136 may be varied according to the concentration of the bio materials 136 put into the reaction vessels 120. That is, if the concentration of the bio materials 136 contained in a solution is low, small aggregations such as the aggregation 150a shown in FIG. 5B may be formed. On the other hand, if the concentration of the bio materials 136 contained in a solution is high, relatively large aggregations such as the aggregation 150b shown in FIG. 5B may be formed.

In addition, as the aggregation of the gold nanoparticles 132 proceeds in the reaction vessels 120, the number of particles having a nano size may be reduced, and the sizes of the aggregations 150a and 150b may increase. As the sizes of the aggregations 150a and 150b increase, light scattering at the surfaces of the gold nanoparticles 132 reduces, and thus the surface absorbance of the gold nanoparticles 132 reduces. That is, as the concentration of the bio materials 136 increases, since the binding between bio sensing materials 134 and the bio materials 136 is increased, the possibility of screening the gold nanoparticles 132 with the bio materials 136 is increased. Therefore, the amount of light absorbed at the surfaces of the gold nanoparticles 132 is reduced.

In other words, according to the concentration of the bio materials 136, the size of the aggregations 150a and 150b can be varied, and the surface absorbance of the gold nanoparticles 132 can be varied according to the size of the aggregations 150a and 150b. Therefore, the concentration of the bio materials 136 can be measured by analyzing variations of the surface absorbance of the gold nanoparticles 132.

That is, after detecting the bio materials 136 by measuring variations of the surface absorbance of the gold nanoparticles 132, the concentration of the bio materials 136 is measured by analyzing the variations of the surface absorbance. In detail, the concentration of the bio materials 136 can be measured by analyzing the difference between surface absorbances of the gold nanoparticles 132 at the same wavelength of light before and after the bio materials 136 are bound to the bio sensing materials 134. That is, the concentration of the bio materials 136 can be quantitatively measured by analyzing the difference between surface absorbances of the gold nanoparticles 132 with respect to the wavelength of light before and after the bio materials 136 are bound to the bio sensing materials 134.

Figure 6:
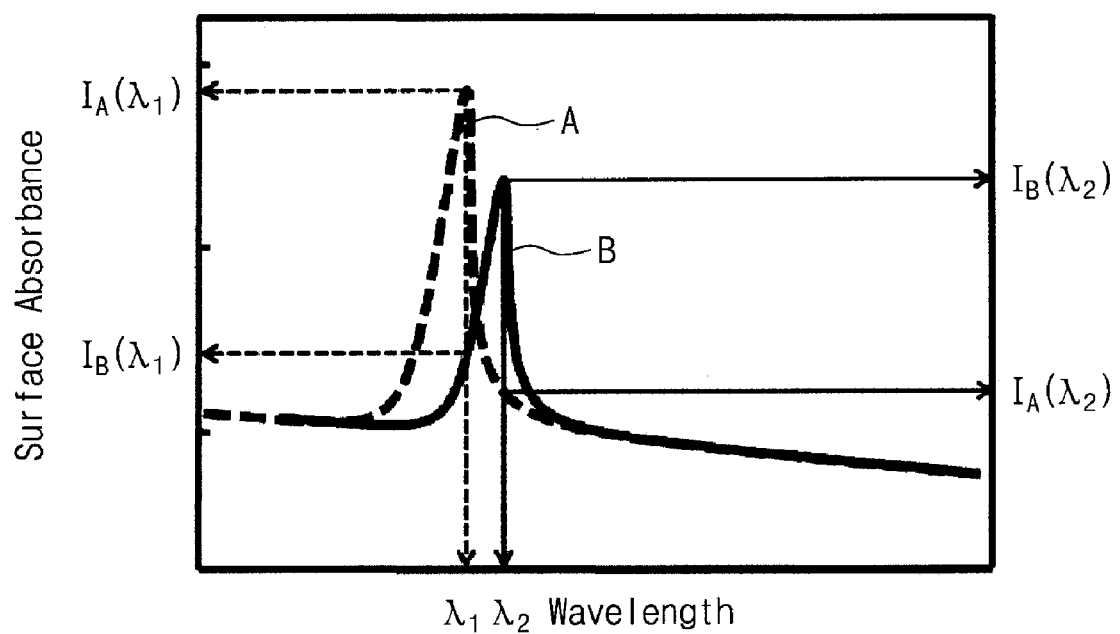
FIG. 6 is a graph illustrating variations of the surface absorbance of gold nanoparticles before and after bio materials are bound to bio sensing materials in a method for detecting bio materials according to an embodiment of the present invention.

FIG. 6 is a graph illustrating the surface absorbance of gold nanoparticles with respect to the wavelength of light before and after bio materials are bound to bio sensing materials in a method for detecting bio materials according to an embodiment of the present invention.

Referring to FIG. 6, the dashed curve A represents the surface absorbance of gold nanoparticles before bio materials are bound to bio sensing materials, and the solid line B represents the surface absorbance of the gold nanoparticles after the bio materials are bound to the bio sensing materials.

When the curves A and B are compared, the peak wavelength of light is shifted after the bio materials are bound to the bio sensing materials. That is, the peak wavelength of light is varied according to materials bound to the surfaces of the gold nanoparticles. In addition, the surface absorbance of the gold nanoparticles is varied after the bio materials are bound to the bio sensing materials. Therefore, the bio materials can be detected by analyzing the difference between the surface absorbance $I_A(\lambda_1)$ of the gold nanoparticles at a first peak wavelength $\lambda_1$ before binding of the bio materials and the surface absorbance $I_B(\lambda_2)$ of the gold nanoparticles at a second peak wavelength $\lambda_2$ after the binding of the bio materials. Here, the first and second peak wavelengths $\lambda_1$ and $\lambda_2$ are center wavelengths of light detected by a detecting unit when surface absorbances are measured using the detecting unit before and after binding of the bio materials. That is, bio materials can be detected by measuring variations of surface absorbance (i.e., light intensity) before and after the bio materials are bound to bio sensing materials.

In addition, the concentration of the bio materials can be quantitatively measured by analyzing the difference between the surface absorbances $I_A(\lambda_1)$ and $I_B(\lambda_2)$ at the first and second center wavelengths $\lambda_1$ and $\lambda_2$ before and after the binding of the bio materials to the bio sensing materials. That is, the concentration of the bio materials can be quantitatively measured by analyzing the surface absorbance differences $(I_A(\lambda_1)-I_B(\lambda_1))$ and $(I_B(\lambda_2)-I_A(\lambda_2))$.

As described above, according to the apparatus for detecting bio materials and the method for detecting bio materials by using the apparatus, the existence of bio materials and the concentration of the bio materials can be determined by measuring variations of the surface absorbance of gold nanoparticles caused by reaction between the bio materials and bio sensing materials on the gold nanoparticles.

According to the apparatus for detecting bio materials in accordance with the present invention, bio materials can be detected using gold nanoparticles, and thus the apparatus can be manufactured with low costs. Furthermore, since light transmitted through the gold nanoparticles is detected by using an optical sensor such as a photodiode, the detecting unit can be small and manufactured with low costs.

In addition, bio materials can be detected independent of the incident angle of light on the gold nanoparticles; that is, bio materials can be easily detected.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An apparatus for detecting bio materials, comprising:
   a bio material reacting unit comprising bio sensing materials immobilized on gold nanoparticles;
   an optical source unit configured to emit light toward the bio material reacting unit; and
   a detecting unit configured to measure variations of surface absorbance of the gold nanoparticles by detecting light transmitted through the bio material reacting unit before and after a bio material is bound to the bio sensing materials.

2. The apparatus of claim 1, wherein the bio material reacting unit comprises:
   a substrate through which light passes; and
   a reaction vessel disposed at the substrate for accommodating the bio sensing materials immobilized on the gold nanoparticles.

3. The apparatus of claim 2, wherein the substrate is formed of a transparent material.

4. The apparatus of claim 2, wherein the reaction vessel is provided in plurality, and bio sensing materials having different characteristics are accommodated in the reaction vessels, respectively.

5. The apparatus of claim 4, wherein the optical source unit comprises a plurality of optical sources corresponding to the reaction vessels, respectively.

6. The apparatus of claim 2, wherein the detecting unit faces the optical source unit, and the bio material reacting unit is disposed between the detecting unit and the optical source unit.

7. The apparatus of claim 1, wherein the detecting unit comprises at least one selected from the group consisting of a photodiode, a phototransistor, a photomultiplier, a CCD (charge coupled device), and a CMOS (complementary metal oxide semiconductor) image sensor.

8. The apparatus of claim 1, wherein the bio sensing materials comprise at least one selected from the group consisting of nucleic acids, cells, viruses, proteins, organic molecules, and non-organic molecules.

9. The apparatus of claim 8, wherein the nucleic acids comprise at least one selected from the group consisting of DNAs, RNAs, PNAS, LNAs, and hybrids thereof.

10. The apparatus of claim 8, wherein the proteins comprise at least one selected from the group consisting of enzymes, matrixes, antigens, antibodies, ligands, aptamers, and receptors.

11. A method for detecting bio materials, comprising:
    immobilizing bio sensing materials capable of binding to a bio material on gold nanoparticles;
    binding bio materials to the bio sensing materials immobilized on the gold nanoparticles;
    illuminating light onto the gold nanoparticles before the binding of the bio materials to the bio sensing materials;
    illuminating light onto the gold nanoparticles after the binding of the bio materials to the bio sensing materials; and
    measuring variations of surface absorbance of the gold nanoparticles by detecting light transmitted through the gold nanoparticles before and after the binding of the bio materials to the bio sensing materials.

12. The method of claim 11, further comprising quantifying concentration of the bio sensing materials by analyzing the variations of the surface absorbance of the gold nanoparticles in the measuring of the variations of the surface absorbance.

13. The method of claim 11, wherein prior to the immobilizing of the bio sensing materials, the method further comprises:
    dispersing the gold nanoparticles in a buffer solution; and
    supplying the bio sensing materials to the gold nanoparticles dispersed in the buffer solution.

14. The method of claim 13, wherein the binding of the bio materials to the bio sensing materials comprises supplying a solution containing the bio materials to the buffer solution containing the bio sensing materials.

15. The method of claim 14, wherein the solution containing the bio materials is blood, blood serum, blood plasma, urine, or saliva.

16. The method of claim 11, wherein the bio sensing materials comprise at least one selected from the group consisting of nucleic acids, proteins, organic molecules, and non-organic molecules.

17. The method of claim 16, wherein the nucleic acids comprise at least one selected from the group consisting of DNAs, RNAs, PNAs, LNAs, and hybrids thereof.

18. The method of claim 16, wherein the proteins comprise at least one selected from the group consisting of enzymes, matrixes, antigens, antibodies, ligands, aptamers, and receptors.

19. The method of claim 11, wherein the binding of the bio materials to the bio sensing materials comprises nucleic acid hybridization, antigen-antibody reaction, or enzyme binding reaction.

\* \* \* \* \*